United States Patent [19]

Forgang et al.

[11] Patent Number: 5,600,246
[45] Date of Patent: Feb. 4, 1997

[54] METHOD AND APPARATUS FOR REDUCING SIGNAL-PHASE ERROR IN INDUCTION WELL LOGGING INSTRUMENTS

[75] Inventors: Stanislav Forgang, Houston; Otto N. Fanini, Stafford, both of Tex.

[73] Assignee: Western Atlas International, Inc., Houston, Tex.

[21] Appl. No.: 563,541

[22] Filed: Nov. 28, 1995

[51] Int. Cl.$^6$ .............................. G01V 3/28; G01V 3/18; G01R 33/12; G01N 27/72
[52] U.S. Cl. ........................................... 324/339; 324/233
[58] Field of Search ..................................... 324/338, 339, 324/340, 341, 342, 343, 233, 326, 327, 328, 329

[56] References Cited

U.S. PATENT DOCUMENTS 4,720,681 1/1988 Sinclair ................................... 324/339

*Primary Examiner*—Walter E. Snow
*Attorney, Agent, or Firm*—Richard A. Fagin

[57] ABSTRACT

An apparatus for calibrating phase response of a receiver in an induction well logging instrument. The apparatus includes a source of alternating current selectively coupled to a transmitter. A low-gain antenna is disposed proximal to the transmitter for generating voltage in response to a magnetic field generated by the alternating current in the transmitter. The instrument includes a receiver spaced apart from transmitter. A phase comparator is coupled at one input to the low-gain antenna and at its other input to the source of alternating current. The phase comparator generates a signal corresponding to phase difference between the voltage in the low-gain antenna, and the alternating current. A sample and hold circuit is coupled to phase comparator for retaining the most recent signal from the phase comparator. A time-delay circuit is coupled to the source of alternating current and to the sample and hold circuit. The time-delay circuit output consists of the alternating current time-shifted by an amount corresponding to the difference in phase. A current switch is interconnected between the output of the delay line and the receiver for selectively injecting the time-shifted alternating current into the receiver. When the time-shifted alternating current is injected into the receiver, the transmitter is turned off. The receiver output and the time-shifted alternating current are coupled to analog to digital converters and a computer for determining the phase difference between the receiver output and the delayed alternating current.

11 Claims, 3 Drawing Sheets

METHOD AND APPARATUS FOR REDUCING SIGNAL-PHASE ERROR IN INDUCTION WELL LOGGING INSTRUMENTS

BACKGROUND OF THE INVENTION

1. Field of the Invention

The present invention is related to the field of electromagnetic induction well logging. More specifically, the present invention is related to methods and apparatus for improving the accuracy of induction well logging instrument by increasing the accuracy with which the phase response of the instrument can be determined and compensated.

2. Description of the Related Art

Electromagnetic induction well logging instrument the used to determine resistivity of earth formations penetrated by wellbores. The induction well logging instrument includes a source of alternating electric current and a transmitter. The transmitter can be a wire coil through which the alternating current is conducted. The alternating current passing through the coil induces corresponding alternating magnetic fields in the earth formations surrounding the wellbore. The induction logging instrument also includes a receiver. The receiver can also be a wire coil, positioned at a spaced apart location from the transmitter. The alternating magnetic fields induced in the earth formation themselves induce alternating eddy current in the earth formation. The magnitude of the eddy currents is related to the conductivity (the inverse of the resistivity) of the earth formations. The eddy current induce alternating voltages in the receiver. Circuits in the induction logging tool measure the magnitude of the voltages induced in the receiver by the eddy current in order to determine the conductivity, and thereby the resistivity, of the earth formation.

A particular difficulty in determining the magnitude of the voltages induced in the receiver by the eddy currents is that the alternating magnetic field from the transmitter itself directly induces voltages in the receiver, these voltages being referred to as direct-coupled voltages. The magnitude of the direct-coupled voltages is typically much greater than the magnitude of the voltages induced by the eddy current. Methods known in the an for reducing the magnitude of the direct-coupled voltages include adding "balancing" coils to the wire coil forming the receiver. The balancing coil is axially positioned relative to the receiver coil, and is series-connected to the receiver coil in inverse polarity, so that a substantial portion of the direct-coupled voltages can be cancelled. In order for the balancing coil to function correctly, it is necessary to build the receiver coil and the balancing coil with a very high degree of geometric precision, and preferably design the coils so as to be highly resistant to changes in geometry and electrical response characteristics as the ambient pressure and temperature to which the coils are exposed changes. Induction well logging instruments are typically exposed to very large variations in pressure and temperature, so design of the receivers and balancing coils is difficult and expensive.

Another technique known in the art for reducing the effect of the direct-coupled voltages is to conduct the output of the receiver to a phase sensitive detector. A phase sensitive detector measures the magnitude of an alternating voltage which is in phase with a phase reference signal. In the induction well logging instrument, the direct-coupled voltages are typically 90 degrees out of phase with the magnetic field created by the alternating current flowing in the transmitter coil. The eddy currents typically lag the transmitter's magnetic field by a 90 degree phase difference. The voltages induced in the receiver coil by the eddy currents lag the eddy currents by a 90 degree phase difference and therefore are typically 180 degrees out of phase with respect to the transmitter's magnetic field. The phase sensitive detector is adapted to measure the magnitude of voltages in the receiver which are exactly 180 degrees out of phase with respect to the current flowing through the transmitter coil. The source of alternating current can be electrically coupled to the phase sensitive detector to provide a phase reference for the phase sensitive detector. However, the phase response of the transmitter itself may not be constant, or may not be precisely known. The phase response of the transmitter affects the degree of time coincidence between the magnitude of the alternating current generated by the source and the magnitude of the magnetic field induced in the earth formation by the current passing through the transmitter coil. If the phase sensitive detector is phase-referenced only to the source of alternating current, then variations in phase response of the transmitter could affect the accuracy with which the phase sensitive detector can determine the magnitude of the eddy current induced voltages in the receiver coil. The direct-coupled voltages induced by the transmitter's magnetic field are typically much larger than the eddy current induced voltages. The direct-coupled voltages may still have a large amplitude relative to the eddy current induced voltages at only a few degrees from 180 degrees phase separation from the transmitter's magnetic field. Small differences in the phase reference, with respect to the phase of the transmitter's magnetic field, when used for the phase sensitive detector can therefore result in large errors in the measurement of the eddy current induced voltages in the receiver.

To overcome the preceding limitation in the induction logging instrument, it is known in the art to provide an additional, low-gain antenna (which can be a wire coil) near the transmitter to measure directly the magnitude of the magnetic field generated by the transmitter. The transmitter's magnetic field induces voltages directly into the additional antenna. The voltages induced directly in the low-gain antenna are substantially time correspondent with the magnetic field generated by the transmitter current. The voltages induced in the low-gain antenna can be used as a phase reference for the phase sensitive detector when shifted by 90 degrees.

A limitation to using the low-gain antenna is that the phase response of the receiver coil, and analog amplifiers which are typically connected to the receiver coil, may not be precisely known. The receiver coil may have variations in phase response to voltage inducted by the eddy currents. Variation in phase response can cause the eddy current induced voltage in the receiver coil not to be always precisely 90 degrees out of phase with the eddy current magnitude. Analog amplifiers are typically connected to the receiver coil to increase the magnitude of the voltages induced in the receiver coil to a level compatible with the signal input range of the phase sensitive detector or an analog-to-digital converter. If the phase sensitive detector is referenced only to the transmitter's magnetic field, then variations in the combined phase response of the receiver and the analog amplifier can result in error in determining the magnitude of the voltages induced in the receiver by the eddy current.

U. S. Pat. No. 4,720,681 issued to Sinclair describes a system for calibrating the phase response of the analog amplifier connected to the receiver coil (the "receiver amplifier"). The system described in the Sinclair '681 patent includes a switch for momentarily conducting a portion of the current supplied to the transmitter to the input of the receiver amplifier. Phase response of the receiver amplifier can be compared to the transmitter current reference to calibrate the receiver amplifier phase response.

A drawback to the system disclosed in the Sinclair '681 patent is that it only calibrates the receiver amplifier. The receiver coil is switched out of the receiver circuit during calibration. The phase response of the receiver coil itself remains uncalibrated. The phase response of the receiver coil becomes increasingly important at higher operating frequencies contemplated by more modern induction logging tools. Another drawback to the system disclosed in the Sinclair '681 patent is that is uses the transmitter current for a phase reference. At low alternating current frequencies, typically less than about 40 KHz, the phase response of the transmitter has an insignificant effect on the accuracy with which the alternating current may be used as a phase reference for the phase sensitive detector. At higher alternating current frequencies, the phase response of the transmitter can have a significant effect on the accuracy of the alternating current as a phase reference.

Accordingly, it is an object of the present invention to provide an improved system and method for determining and compensating for variations in the phase response of the transmitter, the receiver coil and analog amplifier in an induction well logging instrument.

SUMMARY OF THE INVENTION

The present invention is an apparatus for calibrating phase response of a receiver in an electromagnetic induction well logging instrument. The apparatus includes a source of alternating current operably coupled to a transmitter. A low-gain antenna is positioned proximal to the transmitter for generating a voltage in response to a magnetic field created by passing the alternating current through the transmitter. The instrument includes a receiver spaced apart from the transmitter. A phase comparator is electrically coupled at one input to the low-gain antenna and at its other input the phase comparator is coupled to the source of alternating current. The phase comparator is for generating a signal corresponding to a difference in phase between the voltage generated in the low-gain antenna, and the source of alternating current. A sample and hold circuit is coupled to the output of the phase comparator retaining the most recently measured one of the signals generated by the phase comparator. A time-delay circuit is coupled to the source of alternating current and to the sample and hold circuit. The time-delay circuit provides an output consisting of the alternating current time-shifted by an amount corresponding to the difference in phase measured by the phase comparator. A current switch is interconnected between the output of the time-delay circuit and the receiver for selectively injecting the time-shifted alternating current into the receiver. When the time-shifted alternating current is injected into the receiver, a controller selectively disconnects the source from the transmitter. The receiver output and the time-shifted alternating current are coupled to analog to digital converters and a computer to determine the phase difference between the receiver output and the time-shifted alternating current.

In a preferred embodiment of the invention, the source of alternating current includes a read only memory programmed with a series of numbers corresponding to the alternating current waveform, a digital to analog converter to convert the numbers to the magnitudes of the alternating current, and a low pass filter to remove stair step noise which is an artifact of the digital to analog conversion.

The present invention further includes a method for determining the phase response of a receiver in an electromagnetic induction well logging instrument. The method includes the steps of generating an alternating current, conducting the alternating current through a transmitter to induce an alternating magnetic field around the transmitter, and inducing voltages in a low gain-antenna proximal to the transmitter. The voltages are substantially time correspondent with the magnetic field. The method then includes measuring a difference in phase between the induced voltages and the alternating current, delaying a portion of the alternating current by a time corresponding to the difference in phase so measured, momentarily stopping the alternating current from flowing through the transmitter, and conducting the delayed portion of the alternating current through a receiver spaced apart from the transmitter. Phase difference is measured between the delayed portion of the alternating current and an output of the receiver to determine the phase response of the receiver.

DESCRIPTION OF THE PREFERRED EMBODIMENT

Figure 1:
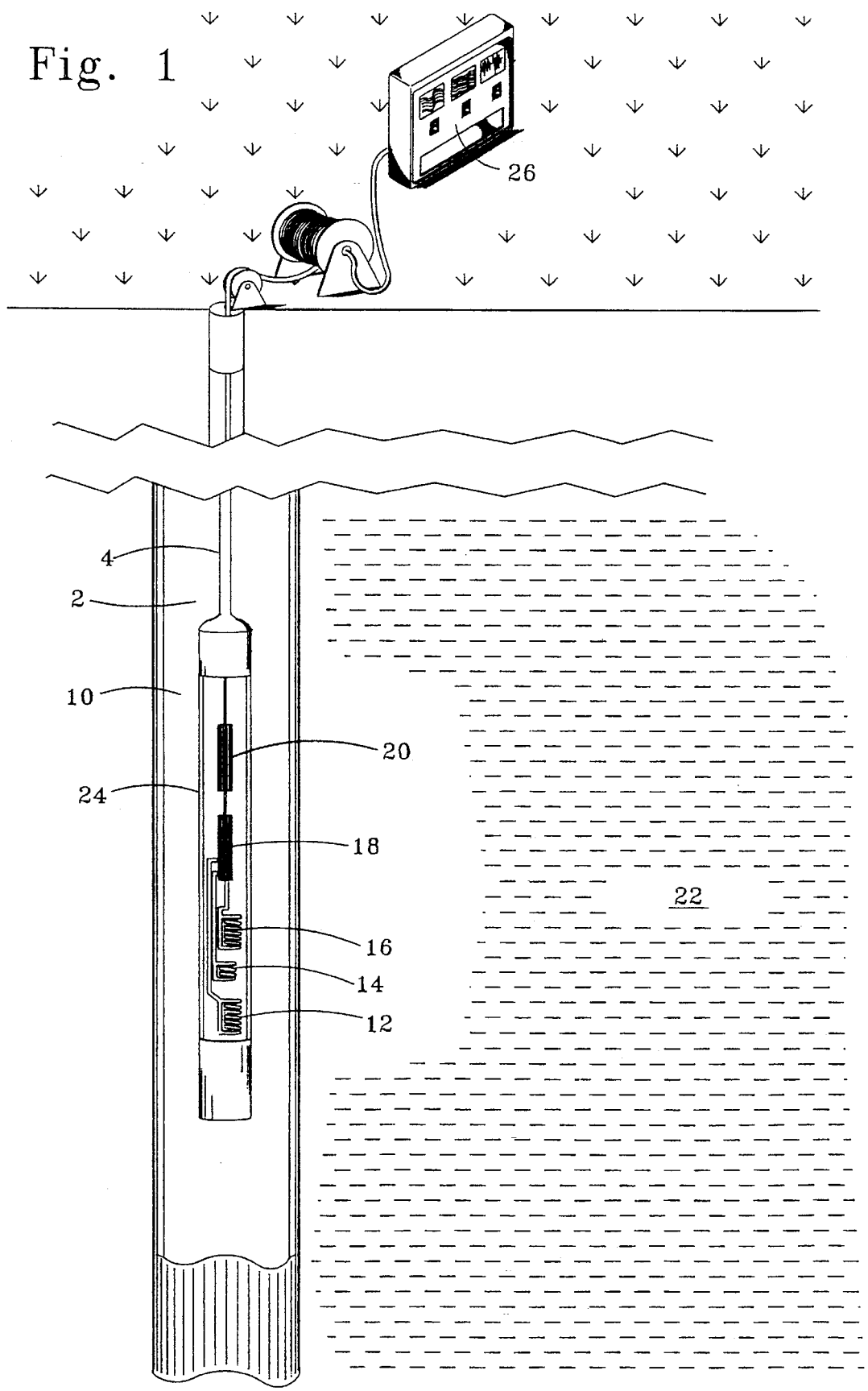
FIG. 1 shows an induction well logging tool inserted into a wellbore drilled through earth formations.

FIG. 1 shows an induction logging tool 10 inserted into a wellbore 2 drilled through earth formations 22. The induction logging tool 10 typically includes an elongated sonde 24. Active components of the tool 10, which will be further explained, are typically located within the interior of the sonde 24. The tool 10 can be lowered into and withdrawn from the wellbore 2 by means of an armored electrical cable 4 attached to the tool 10. The cable 4 can include at least one insulated electrical conductor (not shown separately) for transmitting electrical power to the tool 10 and for communicating signals from the tool 10 to a recording unit 26 disposed at the earth's surface.

The active components of the tool 10 typically include a transmitter 12. The transmitter 12 can comprise a wire coil, and as is understood by those skilled in the art can also comprise a plurality of wire coils positioned at axially spaced apart locations along the sonde 24.

The active components of the tool 10 also include a receiver 16, which can also be a wire coil. As is understood by those skilled in the art, the receiver 16 can also comprise a plurality of wire coils positioned at spaced apart locations. The receiver 16 is typically positioned at a spaced apart location from the transmitter 12. The spacing between the transmitter 12 and the receiver 16 depends on the radial depth, within the earth formations 22, that investigation of the electrical properties of the earth formations 22 is desired by the system designer. Methods for determining the spacing between the transmitter 12 and the receiver 16 are known in the art.

The receiver 16 and the transmitter 12 are electrically connected to a signal generator/processor 18, the operation of which will be further explained. The tool 10 in the present invention also includes a low-gain antenna 14 which can be positioned proximal to the transmitter 12. A magnetic field is generated by an alternating electrical current passing through the transmitter 12. This magnetic field in turn induces voltages in the low-gain antenna 14. The voltages induced in the low-gain antenna correspond to the strength of the magnetic field surrounding the transmitter 12. The voltages induced in the low-gain antenna 14 are coupled to one input of a synchronizer 40. Operation of the synchronizer 40 will be further explained.

The signal generator/processor 18 provides data signals to a telemetry unit 20. The data signals correspond to the magnitude of voltages induced in the receiver 16 as a result of the magnetic field and as a result of eddy currents induced in the formations 22 by the magnetic field. The telemetry unit 20 can transmit the data signals to the recording unit 26 for recording and observation. Alternatively, the telemetry unit 20 can include a recording device such as a digital memory (not shown separately in FIG. 1) for storing the data signals until needed by the system operator.

As is understood by those skilled in the art, alternating electrical current, which can be generated in the generator/processor 18, can be conducted through the transmitter 12. Passing the alternating current through the transmitter 12 generates an alternating magnetic field in the earth formations 22 around the transmitter 12. The alternating magnetic field in turn induces eddy currents in the earth formations 22. The magnitude of the eddy currents is related to the conductivity of the earth formations 22. The eddy currents are typically shifted in phase by 90 degrees with respect to the magnetic field generated by the alternating current passing through the transmitter 12. The eddy currents themselves induce voltages in the receiver 16. The voltages induced in the receiver 16 by the eddy currents typically are phase shifted 90 degrees with respect to the eddy currents. The voltages induced in the receiver 16 by the eddy currents are therefore 180 degrees out of phase with the magnetic field. The phase relationship of the eddy current induced voltages in the receiver 16 enables resolving those voltages even in the presence of voltages which are directly induced in the receiver 16 by the magnetic field. Directly induced voltages are typically 90 degrees phase-shifted with respect to the magnetic field. As is understood by those skilled in the art, the magnitude of the directly induced voltages is typically much greater than the eddy current induced voltages. Resolving the eddy current induced voltages in the presence of the directly induced voltages requires that the receiver 16 voltage be measured within a precisely known phase relationship with respect to the magnetic field. In order to determine the phase relationship of the receiver 16 voltage with respect to the magnetic field, the phase response of the transmitter 12 and the receiver 16 must be calibrated. The means by which the present invention calibrates the phase response of the transmitter 12 and receiver 16 will be further explained.

Figure 2:
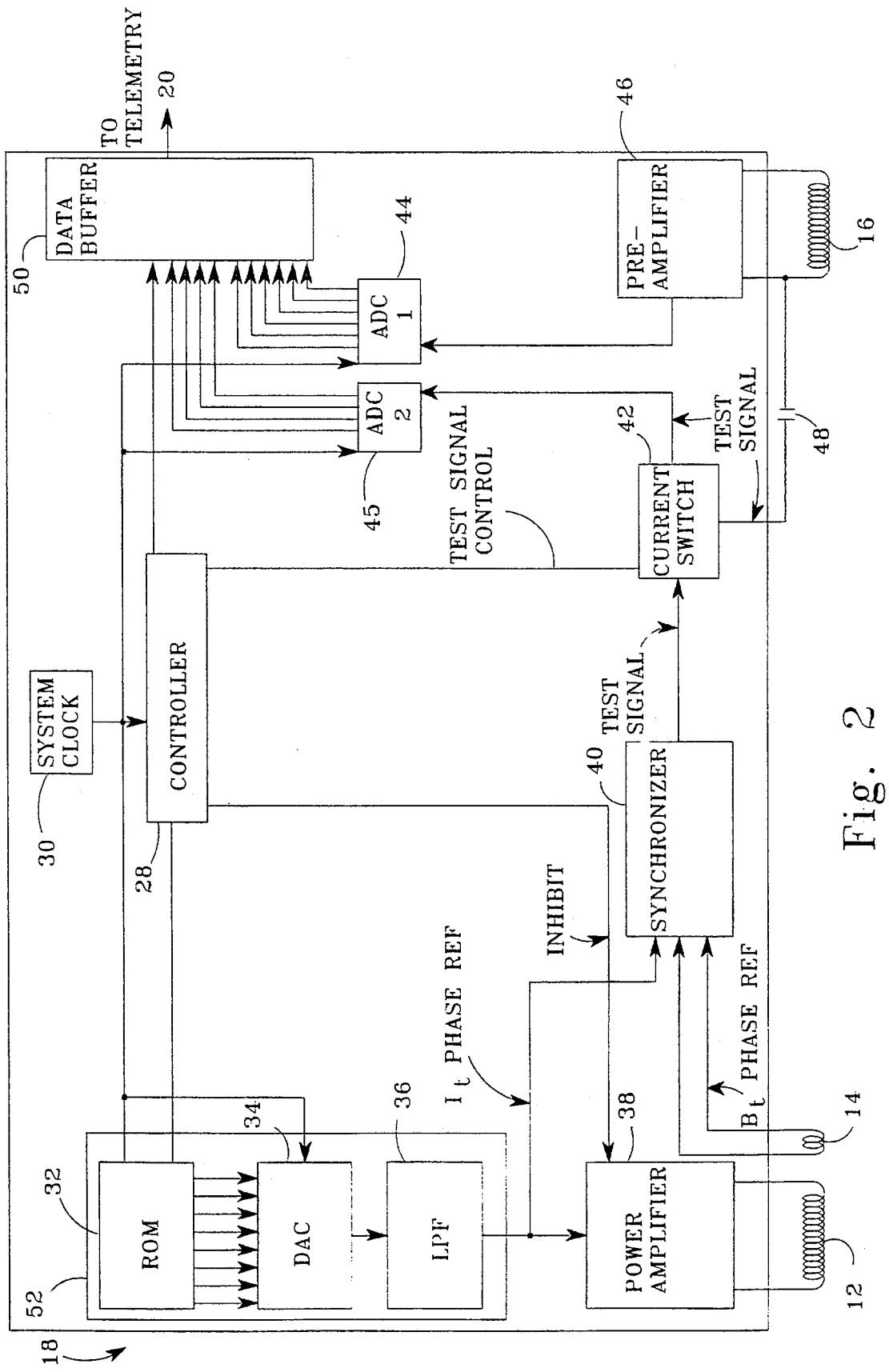
FIG. 2 shows a signal generator/processor according to the present invention.

FIG. 2 shows the generator/processor 18 in more detail. The alternating current used to drive the transmitter 12 can be generated by a signal generator, shown generally at 52. In a preferred embodiment of the invention, the signal generator 52 can include a read-only memory (ROM) 32. The ROM 32 can be programmed with a series of digital words corresponding to the magnitude of the alternating current at spaced-apart time intervals. The ROM 32 is timed by a system clock 30, and is programmed to transmit sequentially, at time intervals determined by the rate of the system clock 30, each of the words in the series to a digital to analog converter (DAC) 34. The DAC converts the words into corresponding analog voltage levels. High-frequency "stair-step" noise is typically present in the output of the DAC 36 as an artifact of the digital to analog conversion. The stair step noise can be substantially removed by including a low pass filter (LPF) 36 coupled to the output of the DAC 34. The output of the LPF 36 comprises an alternating voltage substantially representing the analog waveform of the alternating current which drives the transmitter 12.

The output of the LPF 36 can be coupled to the input of a power amplifier 38. The output of the power amplifier 38 is electrically coupled to the transmitter 12 and provides the current to the transmitter 12 necessary to generate the magnetic field. The power amplifier 38 includes a feature enabling the amplifier 38 to be inhibited on receipt of a control signal from a system controller 28, which will be further explained.

In the present invention, the series of words stored in the ROM 32 can represent a sinusoidal waveform. It is to be understood that any other waveform desired by the system designer which can be used for induction logging, such as a square wave, could also have corresponding digital words programmed into the ROM 32. It is to be understood that the choice of waveform is a matter of convenience for the system designer and is not to be construed as a limitation on the invention.

It is also to be understood that the signal generator 52 in the present embodiment of the invention is not limited to the digital embodiment as disclosed herein. An analog oscillator of a type familiar to those skilled in the art could also perform the required function of the signal generator 52 of the present invention. The embodiment of the signal generator 52 is a matter of convenience for the system designer and is not to be construed as a limitation on the invention.

The signal generator 52 typically can generate alternating current within a frequency range of about 10 KHz to about 2 MHz. The nature of the response of the tool 10 at different frequencies is known in the art. The frequency of the alternating current is a matter of convenience for the system designer and is not to be construed as a limitation on the invention.

The output of the LPF 36 can also provide a phase reference for the alternating current flowing through the transmitter 12. The output of the LPF 36 which is used as a phase reference can be coupled to one phase reference input of the synchronizer 40. The other phase reference input of the synchronizer 40 is electrically coupled to the low gain antenna 14. The magnetic field generated by the current passing through the transmitter 12 induces voltages in the low gain antenna 14. The voltages induced in the low gain antenna 14 are substantially time-correspondent with the magnetic field generated by the transmitter 12, and therefore the voltages induced in the low gain antenna 14 can be used as a phase reference for the magnetic field generated by the transmitter 12. The synchronizer 40 measures any difference in phase between the magnetic field, at one input, and the alternating current flowing through the transmitter 12, provided to the other input from the LPF 36. Differences between the phase of the magnetic field and the phase of the alternating current can be caused by variations in the phase response of the transmitter 12.

The phase difference measurements made by the synchronizer 40 can be used to generate a test current having a phase substantially matched to the phase of the magnetic field of the transmitter 12, even when the alternating current to the transmitter 12 is turned off, as will be further explained. This test current can be periodically conducted to the receiver 16 to calibrate the phase response of the receiver 16.

Figure 3:
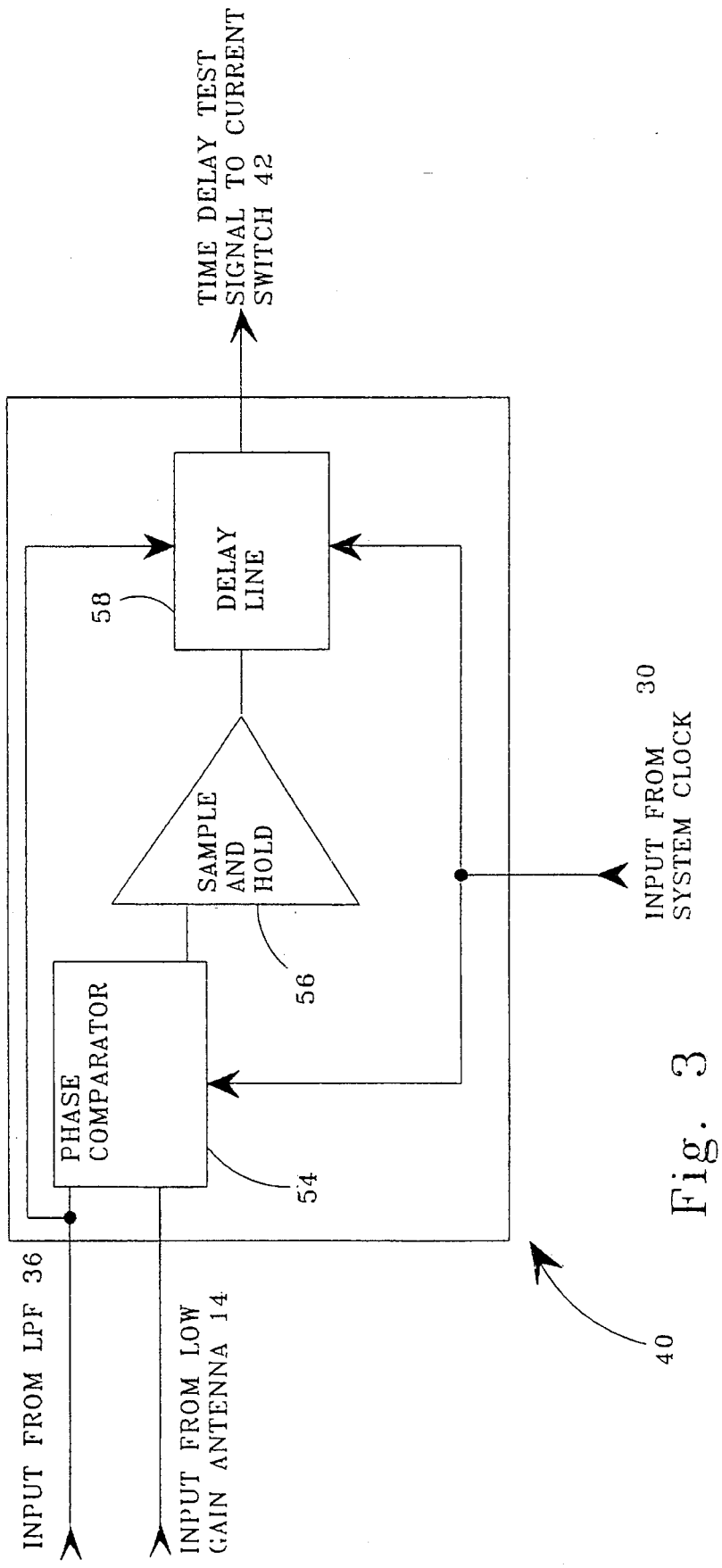
FIG. 3 shows the synchronizer of the present invention in more detail.

Operation of the synchronizer 40 can be better understood by referring to FIG. 3. The synchronizer 40 can include, for example, a phase comparator 54 timed by the system clock 30. The phase comparator 54 measures the difference between the phase of the alternating voltage input from the LPF 34 and the phase of the magnetic field, as detected by the low-gain antenna 14. The output of the phase comparator 54 can be a voltage proportional to the phase difference between the signals at its two inputs. The output of the phase comparator 54 can be conducted to a sample and hold circuit 56. The sample and hold circuit 56 retains the voltage which was last output by the phase comparator 54 for use when the current to the transmitter (12 in FIG. 2) is turned off, and no output is generated by the phase comparator 54.

The output of the sample and hold circuit 56 provides a control signal to a delay line 58. The control signal causes the delay line 58 to time shift the alternating voltage from input the LPF (36 in FIG. 2) by an amount exactly correspondent to the amount of phase shift measured by the phase comparator 54. The output of the delay line 58 forms the previously described test signal, which can be an alternating voltage substantially phase coincident with the magnetic field generated by the transmitter 12. The test signal is conducted to a current switch (42 in FIG. 2). If the power amplifier (38 in FIG. 2) is momentarily inhibited, the reason for which will be further explained, the output of the delay line 58 will still comprise the alternating voltage input from the LPF 36, time-delayed by the most recently measured value of phase difference measured in the phase comparator 54 because the sample and hold circuit 56 retains the voltage corresponding to that most recently measured phase shift and conducts that voltage to the delay line 58. A test signal which is substantially phase coincident with the magnetic field can therefore be generated even in the temporary absence of the magnetic field.

The means by which the present invention calibrates the phase response of the receiver 16 can be better understood by referring once again to FIG. 2. The phase response of the receiver 16 can be periodically calibrated by conducting the previously described test signal into a circuit formed by the receiver 16 and by the input of a preamplifier 46 coupled to the receiver 16. The purpose of the preamplifier 46 will be further explained. During the time the receiver 16 is to be calibrated, it is desirable to turn off the alternating current flowing through the transmitter 12 so that the receiver 16 response to the test signal will not be masked by voltages induced in the receiver 16 by the eddy currents induced in the earth formation (22 in FIG. 1) or by the directly induced voltage. The test signal is controllably conducted to the receiver 16 circuit by the current switch 42. The current switch 42 and the power amplifier 38 can be controlled by the system controller 28. In the present embodiment, the system controller 28 can be a microprocessor such as a unit made by Intel Corp. and sold under model designation 186EB. At a time at which the receiver 16 is to be calibrated, programming instructions resident in the controller 28 can cause the controller 28 to send an inhibit command to the power amplifier 38. The alternating current then stops flowing through the transmitter 12, and therefore the magnetic field substantially disappears and eddy currents are no longer induced in the earth formation 22. The induced voltage level in the receiver 16 substantially drops to zero. The signal generator 52, however, continues to operate. The test signal can still be output from the synchronizer 40. The sample and hold circuit (56 in FIG. 3) in the synchronizer 40 retains the most recently made measurement of the phase difference between the magnetic field and the alternating current from the signal generator 52. The delay line (58 in FIG. 3) in the synchronizer 40 will cause the alternating voltage input from the generator 52 to be time delayed, as previously explained, by an amount corresponding to the most recently measured phase shift before the power amplifier 38 was inhibited. The controller 28 then actuates the current switch 42 so that the time-delayed alternating voltage, this being the previously described test signal, can be conducted to the receiver 16 circuit.

The output of the current switch 42 is preferably coupled to the receiver 16 circuit through a capacitor 48. The capacitor 48 should have a reactance value much greater, typically 100 times or more larger, than the reactance of the receiver 16. By proper selection of reactance in the capacitor 48, the test signal will only be changed in phase upon injection into the receiver 16 circuit by the phase response of the receiver 16 circuit.

The preamplifier 46 magnifies the voltage level of the receiver 16 output to be compatible with the input range of a first analog to digital converter (ADC) 44. The output of the first ADC 44 can be conducted to a data buffer 50 to await transmission to the recording unit (26 in FIG. 1) by the telemetry unit (20 in FIG. 1). During times when the power amplifier 38 is turned on, the transmitter 12 generates the magnetic field and the output of the first ADC represents magnitudes of eddy current induced and directly induced voltages, sampled at spaced apart time intervals. During times when the power amplifier 38 is turned off, the output of the first ADC 44 represents the magnitude of the test signal sampled at spaced apart time intervals.

As is shown in FIG. 2, the first ADC 44, the controller 28, the system clock 30, and the signal generator 52 are all timed by the system clock 30. By timing the analog to digital conversion of voltages in the receiver 16 to the same clock signal as the signal generator 52, phase comparison of the test signal after it has passed through the receiver 16 is greatly simplified. During the calibration of the receiver 16, the controller 28 can instruct the first ADC 44 to "tag" a subsequent set of digital words output from the first ADC 44 to indicate that these digital words represent a test signal calibration. The system clock 30 preferably times the first ADC 44 to generate at least four digital words for each full cycle of the alternating current. The individual digital samples are made in the first ADC 44 each at the same corresponding time within each cycle of the alternating voltage output by the generator 52. The time relationship of any digital sample from the ADC 44 with respect to the phase of the generator 52 output is therefore immediately determinable. In the present embodiment of the invention, the controller 28 can initiate transfer of digital words from the ROM 32 to the first DAC 34, thereby initiating the alternating voltage cycle in the signal generator 52. Since the controller 28 initiates the alternating voltage cycle, the controller 28 can internally retain a phase reference for the alternating current used to drive the transmitter 12.

The output of the synchronizer 40, comprising the test signal, can also be conducted to a second ADC 45. The second ADC 45 can also be timed to the system clock 30 so as to generate at least four digital words for each cycle of the alternating current. Digital words generated by the second ADC 45 can be timed to be substantially time coincident with the digital words generated by the first ADC 44. The digital words from the second ADC 45 can also be conducted to the buffer 50.

The digital words from the first ADC 44 represent the magnitude of test signal after it has passed through the receiver 16 and the preamplifier 46. The digital words from the second ADC represent the magnitude of the test signal before it has passed through the receiver 16. The digital words from the second ADC 45 and the first ADC 44 can be transmitted to the recording unit (26 in FIG. 1) for phase comparison. The phase comparison can be performed by a program resident on a computer (not shown) resident in the recording unit 26. The phase comparison program can be of a type familiar to those skilled in the art. Alternatively, the program to perform the phase comparison can reside in the controller 28. The phase difference between the test signal and the output of the preamplifier 46 substantially represents the phase response of the circuit formed by the receiver 16 and the preamplifier 46. As is understood by those skilled in the art, the phase response so determined can be used to improve the accuracy with which the magnitude of the eddy currents induced in the receiver 16 can be determined.

After correction for phase response of the receiver 16 and preamplifier 46, the magnitude of voltages induced in the receiver 16 can be determined at exactly 180 degrees phase lag from the phase of the magnetic field to determine the magnitude of the eddy current. Means by which the digital words stored in the buffer 50, representing the magnitude of voltages induced in the receiver 16, can be used to determine the magnitude of the eddy currents induced in the receiver 16 are known in the art. One system for determining eddy current magnitude is described for example in U.S. Pat. No. 5,452,761 issued to Beard et al.

The invention disclosed herein provides an improved system and method measuring the magnitudes of eddy-current induced voltages in induction well logging tool receivers. The improvement is provided by generating a phase reference detection of voltages in the receiver which is corrected for the phase response of the transmitter and for the phase response of the receiver. Those skilled in the art may devise different embodiments of the present invention which do not depart from the spirit of the invention disclosed herein. The invention should therefore be limited in scope only by the claims appended hereto.

What is claimed is:

1. An apparatus for determining a phase response of a receiver in an electromagnetic induction well logging instrument, comprising:
   a source of alternating current selectively coupled to a transmitter;
   a low-gain antenna proximal to said transmitter, said low-gain antenna generating a voltage in response to a magnetic field induced by passing said alternating current through said transmitter;
   a receiver spaced apart from said transmitter, said receiver generating a voltage in response to eddy currents induced by said magnetic field in an earth formation surrounding said instrument;
   a phase comparator coupled at one input to said low-gain antenna, said phase comparator coupled at another input to said source of alternating current, said phase comparator for generating a signal corresponding to a difference in phase between said voltage generated in said low-gain antenna and said source of alternating current;
   a sample and hold circuit coupled to an output of said phase comparator, said sample and hold circuit for retaining a most recent one of said signals output from said phase comparator;
   a time-delay circuit coupled to said source of alternating current and to said sample and hold circuit, said time-delay circuit for providing an output comprising said alternating current time-delayed correspondingly to said difference in phase measured by said phase comparator;
   a current switch interconnected between said output of said time-delay circuit and said receiver, said current switch selectively operable to inject said time-delayed alternating current into said receiver;
   a controller for selectively disconnecting said source from said transmitter, said controller for selectively operating said current switch to inject said time-delayed alternating current when said transmitter is disconnected; and
   means for determining a difference in phase between said output of said time-delay circuit and an output of said receiver when said controller operates said current switch to inject said time-delayed alternating current into said receiver.

2. The apparatus as defined in claim 1 wherein said source of alternating current comprises a signal generator including a read only memory, a digital to analog converter and a low-pass filter, said read only memory programmed with a series of numbers corresponding to a waveform of said alternating current.

3. The apparatus as defined in claim 2 wherein said waveform comprises a sinusoid.

4. The apparatus as defined in claim 1 wherein said source of alternating current further comprises a power amplifier interconnected between said signal generator and said transmitter, said power amplifier including an inhibitor for causing said amplifier to stop sending said alternating current to said transmitter on receipt of a command signal from said controller.

5. The apparatus as defined in claim 1 wherein said means for determining phase difference between said output of said delay line and said output of said receiver when said controller closes said current switch further comprises:
   a first analog to digital converter operatively coupled to said receiver, a second analog to digital converter coupled to said output of said delay line, said first and said second analog to digital converters coupled to a system clock, said first and said second analog to digital converters generating substantially synchronous digital samples of corresponding input signals;
   a computer operatively coupled to said first and said second analog to digital converters for numerically determining a phase difference in said digital signal samples.

6. The apparatus as defined in claim 5 wherein said computer forms part of a recording unit electrically coupled to said well logging instrument.

7. The apparatus as defined in claim 5 wherein said computer forms part of said controller.

8. The apparatus as defined in claim 1 wherein said current switch is coupled to said receiver through a capacitive reactance, said capacitive reactance much larger than an inductive reactance of said receiver so that phase of said time-delayed alternating current is affected primarily by said phase response of said receiver.

9. A method for determining a phase response of a receiver in an electromagnetic induction well logging instrument, comprising the steps of:
   generating an alternating current;
   conducting said alternating current through a transmitter to induce an alternating magnetic field around said transmitter;

inducing voltages in a low gain-antenna proximal to said transmitter, said voltages substantially time correspondent with said magnetic field;

measuring a difference in phase between said induced voltages and said alternating current;

delaying a portion of said alternating current by a time corresponding to said difference in phase;

stopping said alternating current from flowing through said transmitter;

conducting said delayed portion of said alternating current through a receiver spaced apart from said transmitter; and measuring a difference in phase between said delayed portion of said alternating current and an output of said receiver.

10. The method as defined in claim 9 wherein said receiver comprises a receiver coil and a preamplifier.

11. The method as defined in claim 9 wherein said step of measuring a difference in phase includes:

digitizing said delayed portion of said alternating current and said receiver signal at substantially identical times; and measuring a time difference between digital signal samples corresponding to substantially the same portion of a signal waveform.

* * * * *